(12) United States Patent
Clarke et al.

(10) Patent No.: US 10,545,080 B2
(45) Date of Patent: Jan. 28, 2020

(54) DETERMINATION OF INTERFACIAL OR SURFACE TENSION

(71) Applicant: SCHLUMBERGER TECHNOLOGY CORPORATION, Sugar Land, TX (US)

(72) Inventors: Andrew Clarke, Haslingfield (GB); Patrice Ligneul, Chaville (FR); Wael Abdallah, Al-Khobar (SA); Mikhail Stukan, Al-Khobar (SA)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 260 days.

(21) Appl. No.: 14/255,680

(22) Filed: Apr. 17, 2014

(65) Prior Publication Data

US 2014/0311229 A1    Oct. 23, 2014

(30) Foreign Application Priority Data

Apr. 22, 2013 (GB) .................................. 1307185.7

(51) Int. Cl.
*G01N 13/02* (2006.01)

(52) U.S. Cl.
CPC ..... *G01N 13/02* (2013.01); *G01N 2013/0241* (2013.01); *G01N 2013/0266* (2013.01)

(58) Field of Classification Search
CPC ........... G01N 13/02; G01N 2013/0241; G01N 2013/0266

(Continued)

(56) References Cited

U.S. PATENT DOCUMENTS

| 4,196,615 A | 4/1980 | Davis |
| 5,394,740 A | 3/1995 | Schramm et al. |

(Continued)

FOREIGN PATENT DOCUMENTS

| DE | 2915956 | 11/1980 |
| EP | 0149500 | 7/1985 |

(Continued)

OTHER PUBLICATIONS

Combined Search and Examination Report of British Application No GB1208366.3 dated Aug. 21, 2012: pp. 1-5.

(Continued)

*Primary Examiner* — Justin Seo
*Assistant Examiner* — Rodney T Frank

(57) ABSTRACT

A method and apparatus for measuring interfacial or surface tension of a first fluid dispersed in a second fluid, the method involving providing at least one substantially spherical droplet or bubble of the first fluid in a flowing stream of the second fluid in a flow channel, followed by passing the flowing stream comprising the droplet or bubble through a constriction in the flow channel, the constriction being sufficiently constricting so as to cause the droplet or bubble to deform away from its substantially spherical shape and measuring and comparing a physical property of the flowing stream both before and after the constriction, wherein the physical property changes as a result of the deformation of the droplet or bubble, and thereby inferring the interfacial or surface tension from the measured physical property.

25 Claims, 3 Drawing Sheets

(58) Field of Classification Search
USPC .................................................... 73/64.48
See application file for complete search history.

(56) References Cited

U.S. PATENT DOCUMENTS

| | | | |
|---|---|---|---|
| 5,542,289 A | 8/1996 | Hool et al. | |
| 8,613,217 B2 | 12/2013 | Colin et al. | |
| 2004/0244382 A1* | 12/2004 | Hagen | F01K 21/047 60/775 |
| 2005/0056313 A1* | 3/2005 | Hagen | B01F 5/0453 137/3 |
| 2007/0006926 A1* | 1/2007 | Prakash | F15C 1/00 137/800 |
| 2009/0019924 A1 | 1/2009 | Nguyen et al. | |
| 2010/0017135 A1 | 1/2010 | Mostowfi | |
| 2010/0170957 A1 | 7/2010 | Clarke | |
| 2010/0279321 A1* | 11/2010 | Chiu | B01L 3/502746 435/7.23 |
| 2011/0197664 A1 | 8/2011 | Colin et al. | |
| 2013/0298649 A1 | 11/2013 | Clarke | |

FOREIGN PATENT DOCUMENTS

| | | |
|---|---|---|
| GB | 2502058 | 11/2013 |
| WO | 2009004314 | 1/2009 |
| WO | 2009125119 | 10/2009 |
| WO | 2013090690 | 6/2013 |

OTHER PUBLICATIONS

Combined Search and Examination Report of Bristish Application No. GB1307185.7 dated Sep. 3, 2013: pp. 1-7.

Gu et al., "Interfacial tension measurements with microfluidic tapered channels," Colloids and Surfaces A: Physicochem. Eng. Aspects, 2011, vol. 389: pp. 38-42.

Manning-Benson et al., "Article No. CS974797: Measurement of Dynamic Interfacial Properties in an Overflowing Cylinder by Ellipsometry," Journal of Colloid and Interface Science, 1997, vol. 189: pp. 109-116.

Sherwood, "Potential flow around a deforming bubble in a Venturi," Internation Journal of Multiphase Flow, 2000, vol. 26: pp. 2005-2047.

* cited by examiner

DETERMINATION OF INTERFACIAL OR SURFACE TENSION

CROSS-REFERENCE TO RELATED APPLICATION

This application claims priority to British Patent Application No. GB1307185.7 filed Apr. 22, 2013, which is incorporated herein by reference in its entirety.

BACKGROUND

Embodiments of the present invention relate to methods for measuring interfacial or surface tension of a first fluid in contact with a second fluid.

Many methods are known that can measure the interfacial tension between two immiscible liquids. Likewise many methods are known for the measurement of the surface tension of a liquid in a gas.

However some liquids contain a variety of dissolved species, which can migrate towards a newly-formed surface or interface with another fluid. For such liquids the surface tension or interfacial tension may change with time, often over short timescales, as the dissolved species migrate towards the newly-formed surface. For example the liquid may contain surface active species, which can migrate to a newly-formed surface and even diffuse across into the other phase. Such species can alter the value of the interfacial or surface tension over time as the species migrates to the surface, this is particularly the case if the dissolved species are surface-active.

For such liquids it is therefore possible to distinguish between a newly-formed interfacial or surface tension, which exists at the moment of formation of a new interface or surface, and an aged interfacial or surface tension, which is arrived at once an equilibrium state is achieved. Additionally it may be of interest to monitor the change in interfacial or surface tension as the surface ages, to obtain information about the dynamics.

However, classic methods of measuring interfacial tension or surface tension tend to rely on obtaining an equilibrium state before measuring the interfacial tension. These methods are therefore not suitable for measuring the evolution of the interfacial or surface tension during short timescales. Such known methods include the Wilhelmy plate method, the de Nouy ring method and the Pendant Drop method. All these methods rely on comparing a gravitational force effect, produced by a difference in density, and inferring the interfacial tension or surface tension. The pendant drop method relies on knowing the densities of the fluids involved, in order to know the gravitational forces at work. The Wilhelmy plate and de Nouy ring are typically used for surface tension measurements, and involve nulling the mass of the probe, such that only an addition force due to surface tension is measured.

More elaborate methods of measuring interfacial and surface tension exist that do not rely on gravitational inference. One known method of measuring interfacial tension or surface tension over short timescales is the Maximum Bubble Pressure method. In this method a capillary containing a first fluid is inserted into a second fluid and the first fluid is pressurized to form a droplet or bubble at the exit of the capillary tube. The maximum pressure required to generate the bubble or droplet indicates the interfacial or surface tension. Furthermore, different rates of generation of the droplets or bubbles allows the measurement of interfacial tension or surface tension for differently aged surfaces to be measured, thus giving an indication of the evolution of the interfacial or surface tension.

However, one problem with this method is that it involves the formation of a three-phase contact line between the two fluids and the end of the capillary tube. Thus, any surface contamination on the end of the capillary tube can influence the result. When being used to measure model systems, where the measurement can be kept clean, this may not be a problem. However, when measuring real systems, for example fluids extracted from the ground—which may comprise a mixture of water, oil and a wide variety of dissolved species—contamination may become a major factor in influencing the result, rendering accurate measurement impossible.

Microfluidic devices have also been employed to measure interfacial tension. However, these devices also involve contact with a solid surface, introducing contamination issues as discussed above.

PCT patent application, WO 2009/125119, describes measuring the interfacial tension between two fluids in a microfluidic environment. The method relies on generating a map of transition points that mark the breakdown of a stream of one fluid into discrete droplets. This method does not involve contact with a surface and so overcomes the problem of surface contamination. However, as the method of measuring interfacial tension relies on the breakdown of a defined stream into a series of droplets, it is not possible to also measure the aged interfacial tension. Rather, the interfacial tension defines the breakup time, and therefore the time of the measurement.

Therefore, there remains a need in the art for a method of measuring interfacial and surface tension that is insensitive to contamination and can provide dynamic measurements for a newly formed interface through to an aged interface.

SUMMARY

In a first aspect, the embodiments of the present invention relate to a method of measuring interfacial or surface tension of a first fluid dispersed in a second fluid, the method involving: providing at least one substantially spherical droplet or bubble of the first fluid in a flowing stream of the second fluid in a flow channel followed by passing the flowing stream comprising the droplet or bubble through a constriction in the flow channel, the constriction being sufficiently constricting so as to cause the droplet or bubble to deform away from its substantially spherical shape, measuring and comparing a physical property of the flowing stream both before and after the constriction, wherein the physical property changes as a result of the deformation of the droplet or bubble; and thereby inferring the interfacial or surface tension from the measured physical property.

In a second aspect, the embodiments of the present invention relate to an interfacial or surface tension measuring apparatus, comprising a flow channel and a substantially spherical droplet or bubble generator, generating at least one substantially spherical droplet or bubble of a first fluid in a second fluid flowing in the flow channel, the flow channel comprising a constriction sufficiently constricting so as to cause the droplet or bubble to deform away from its substantially spherical shape, and a measuring device to measure a physical property of the flowing stream before and after the constriction.

Such measured physical property of the flowing fluid may include a pressure difference across the constriction, a time taken for a droplet or bubble to pass through the constriction and/or the like.

The measurement of pressure difference can be provided by direct measurement, for example by a differential pressure transducer, using a pair of microfluidic pressure transducers such as described in U.S. Patent Pub. No. 20100017135, and/or the like. In some embodiments, the differential pressure measurements are inferred from a measurement of flow velocity through a further flow channel—which by-passes the constriction, but has an effective diameter to be more constricting than the constriction, so that the majority of the flowing fluid passes through the constriction. This configuration ensures that the droplet or bubble passes through the constriction and not the by-pass.

The term "effective diameter" of a non-circular cross-section channel means the diameter of a notional circular cross-section channel that provides the same volumetric flow as the non-circular cross-section channel under the same conditions.

In some embodiments, the by-pass channel is sufficiently narrow so that the ratio of volumetric flow through the constriction to the volumetric flow through the by-pass channel is at least 5:1, preferably at least 10:1, and more preferably at least 50:1. This may be achieved by arranging for the ratio of the effective diameter of the constriction to the effective diameter of the by-pass to be at least 2:1, preferably at least 5:1, more preferably at least 10:1.

In general, the flow rate through the flow channel upstream of the constriction and by-pass will be known. Therefore, in some aspects, the by-pass channel will comprise a flow rate measuring device. The reading from the flow rate measuring device can therefore provide for a determination of the flow rate information through the constriction, i.e., by subtraction of the reading from the total flow rate, which is generally known.

As can be seen, measurement of the flow rate through the by-pass can be employed to infer the pressure difference that exists in the flow channel across the constriction provided that the viscosity of the continuous fluid is known or can be accurately estimated.

As the bubble or droplet approaches/enters the constriction it is deformed and passes through the constriction and after it exits the constriction it returns to its substantially spherical shape. The change in the droplet as it flows through the constriction provides that the pressure in the continuous flowing fluid across the constriction—i.e., pressure measured across the constriction between a section of the low upstream of the constriction and a section of the flow downstream of the constriction—will be affected. Therefore, the change in pressure difference between locations upstream of the constriction and downstream of the constriction as the droplet flows through the constriction are related to the interfacial tension or surface tension of the droplet. This is because such a droplet or bubble will tend to adopt its lowest energy form, which is a spherical shape, wherever possible. Furthermore, the force required to deform such a droplet or bubble away from spherical, i.e., in order to fit through the constriction, is proportional to the interfacial or surface tension. This force required for deformation comes from a combination of the pressure exerted on the droplet or bubble by the surrounding flowing fluid and the viscous drag provided by the surrounding fluid.

Initially, before any droplet or bubble approaches the constriction, the pressure difference across the constriction is governed by that required to maintain fluid flow through the constriction. However, as the droplet or bubble meets the constriction, it has the effect of causing a blockage of the constriction, i.e., by reducing the effective diameter of the constriction for the flowing fluid. This causes an increase in the pressure difference across the constriction, which concomitantly causes deformation of the droplet or bubble.

Once sufficient deformation of the droplet or bubble has occurred, it moves through the constriction in a deformed shape. Once it leaves the constriction it returns to a substantially spherical shape, as this is its natural low-energy shape. This has the effect of reducing the pressure difference across the constriction. As the droplet or bubble moves away from the constriction the pressure difference across the constriction returns again to the initial level.

Thus, the height of the pressure difference peak measured across the constriction can be taken as representing the magnitude of the extra pressure difference needed to cause deformation of the droplet and therefore, with sufficient additional knowledge of the parameters required, the interfacial or surface tension value can be inferred.

However, it will be appreciated that other parameters will determine the change in pressure as the droplet or bubble passes the constriction. These parameters include the diameter of the constriction, the diameter of the droplet or bubble, the viscosity of the fluid in the droplet or bubble and the viscosity of the flowing fluid. In general, however, the interfacial or surface tension measurement method and device may be employed in either a quantitative or qualitative mode. In a quantitative mode, calibration of the device and method can be used to determine the interfacial or surface tension, where a knowledge of the droplet or bubble size and viscosities of the fluids is known.

When a by-pass channel is present, this enables the viscosity of the continuous fluid to be measured when no bubble or droplet is passing through the constriction. This is because the pressure difference and flow rate through the by-pass are known. This, together with the fact that the fluid flow through the by-pass can be taken to be a laminar or a Poisseuille flow, provides for determining the viscosity by the well-known Poisseuille-Stokes equation. Similarly, a flow measurement can be taken in the flow channel, typically far away from the constriction, to provide a flow rate measurement of the fluid in the flow channel.

The diameter of the droplet or bubble can also be inferred by monitoring the duration of the perturbation in the pressure drop across the constriction together with the velocity of the flowing stream. Alternatively, a capacitative or optical gate method may be employed to determine the droplet diameter. In one embodiment, the droplets or bubbles are generated to be substantially the same size and to be produced at a regular frequency.

For further accuracy the viscosity and density of the droplet or bubble should also be known. However, it may not be possible to have accurate information on the two viscosities, or even the droplet size. In this case, the interfacial or surface tension measurement method and device can be operated in a qualitative mode, and such calibration is not necessary.

The qualitative mode is particularly applicable when monitoring a naturally occurring fluid, such as an oil-in-water or water-in-oil two phase mixture. In particular, the qualitative mode is useful when the viscosities and droplet or bubble sizes are not known. In this case, the measured value of the interfacial or surface tension can only be compared in a qualitative way to other measurements. However, this is particularly useful for indicating a rise or a fall in interfacial or surface tension.

Thus, the method and apparatus of the present invention is particularly useful for measuring/determining the interfacial tensions between droplets of water-in-oil or droplets of oil-in-water. For example, in some situations, there may be leakage of surfactant material into an oil and gas fluid stream. The effect of such an introduction of surfactant would be a dramatic drop in interfacial tension. The present invention operating in qualitative mode can therefore provide an early warning of such an introduction of surfactant by detecting a drop in interfacial tension relative to earlier measurements/observations of interfacial tension existing before such introduction of surfactant.

Over time an operator/processor may gain experience/knowledge of what a "normal" range of values for the interfacial tension is, so that any deviation from normal values can be an early warning mechanism of an interfacial or surface tension change.

The method and apparatus of the present invention may in some circumstances work better for smaller droplet sizes. This is primarily because the inertial forces involved during droplet or bubble deformation become less significant in relation to the interfacial or surface forces, as the droplet or bubble size reduces. Thus, in some embodiments, the droplet or bubble size may be in a range from 0.001 mm to 1 mm, more preferably less than 0.5 mm, more preferably less than 0.1 mm, preferably less than 0.05 mm, most preferably less than 0.02 mm.

Likewise, the flow channel may comprise a narrow dimension. For example in some aspects, the flow channel may have an effective diameter of from 0.04 to 2 mm, preferably less than 1 mm, more preferably less than 0.2 mm.

The present method and apparatus may be carried out in a microfluidic device and may comprise a microfluidic flow-focusing device (FFD) to generate the droplets or bubbles of the first fluid in the second fluid. FFDs can be operated in either pressure control mode or flow rate control mode. However, flow rate control mode can take many minutes to settle to a steady state and hence a pressure controlled system is preferable.

In such an arrangement the droplet or bubbles may be created in a very short timescale and may generate droplets at a rate of up to several 1000/s. The timescale and/or bubble production rate may be varied as required. The fast rate may be used to produce extremely well-defined near-spherical droplets with a diameter variation of <2%.

As will be appreciated, the time taken between droplet or bubble formation can be varied by altering the distance between the point of droplet or bubble formation and the constriction. For example, if the interfacial or surface tension of a newly formed surface is desired then the constriction should be as close as possible to the droplet of bubble formation point, but not so close as to affect or be affected by the droplet or bubble formation process. Likewise, in certain embodiments, if the interfacial or surface tension of an aged surface is desired then the constriction may be disposed far away/at a distance from the droplet or bubble formation point, so that the surface has time to age before a measurement is made.

In one arrangement, the device or method may involve a second constriction downstream from the first constriction. Such a second constriction may perform the same function as the first constriction, but may measure the interfacial or surface tension at a later point in time. Thus, with two such constrictions, it is possible to measure both the interfacial or surface tension of both the newly formed surface and the aged surface, or anything in between.

In one embodiment of the present invention, the first fluid may be separated out from/or provided separately from the second fluid. Each fluid may then be pumped separately into the device. However, as such two-phase liquid systems may comprise naturally occurring two-phase liquid systems, such as oil and water mixtures, it may be difficult to obtain complete separation easily. However the present invention can still provide meaningful results without such complete separation of the phases.

BRIEF DESCRIPTION OF THE DRAWINGS

The present disclosure will now be illustrated by reference to the following figures in which.

Figure 1:
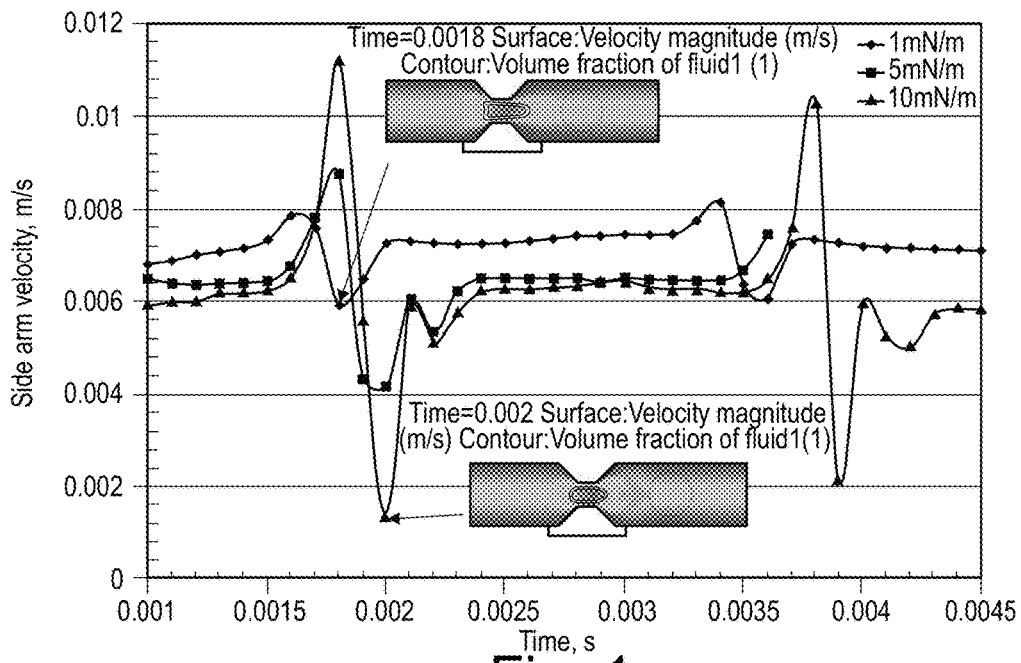
FIG. 1 is a chart of pressure difference across a constriction versus time, in accordance with an embodiment of the present invention.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DESCRIPTION

The ensuing description provides preferred exemplary embodiment(s) only, and is not intended to limit the scope, applicability or configuration of the invention. Rather, the ensuing description of the preferred exemplary embodiment (s) will provide those skilled in the art with an enabling description for implementing a preferred exemplary embodiment of the invention. It being understood that various changes may be made in the function and arrangement of elements without departing from the scope of the invention as set forth in the appended claims.

Specific details are given in the following description to provide a thorough understanding of the embodiments. However, it will be understood by one of ordinary skill in the art that the embodiments maybe practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "computer-readable medium" includes, but is not limited to portable or fixed storage devices, optical storage devices, wireless channels and various other mediums capable of storing, containing or carrying instruction(s) and/or data.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium such as storage medium. A processor(s) may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc., may be passed, forwarded, or transmitted via any suitable means including memory sharing, message passing, token passing, network transmission, etc.

In order to quantify the possible expected behavior of a droplet passing a constriction, a pseudo three dimensional ("3D") finite element calculation was carried out using a modeling program, such as Comsol Multiphysics. Drops of varying interfacial tension were examined as well as drops of varying sizes. The model used a two dimensional ("2D") model with an effective body force to simulate the effect of the third dimension. A phase field formulation was used to track the two liquid phases. The drop being analyzed was initialized just downstream of the orifice and the flow was calculated with periodic boundary conditions, such as the drop exiting the channel at the right re-entered at the left.

FIG. 1 shows the outer liquid velocity in a by-pass channel that allows leakage around the central constriction. The flow in the by-pass channel can be sensed, e.g., by hot wire anemometer. As can be seen in the figure, a distinct relation exists between the observed flow perturbation and interfacial tension.

Figure 2:
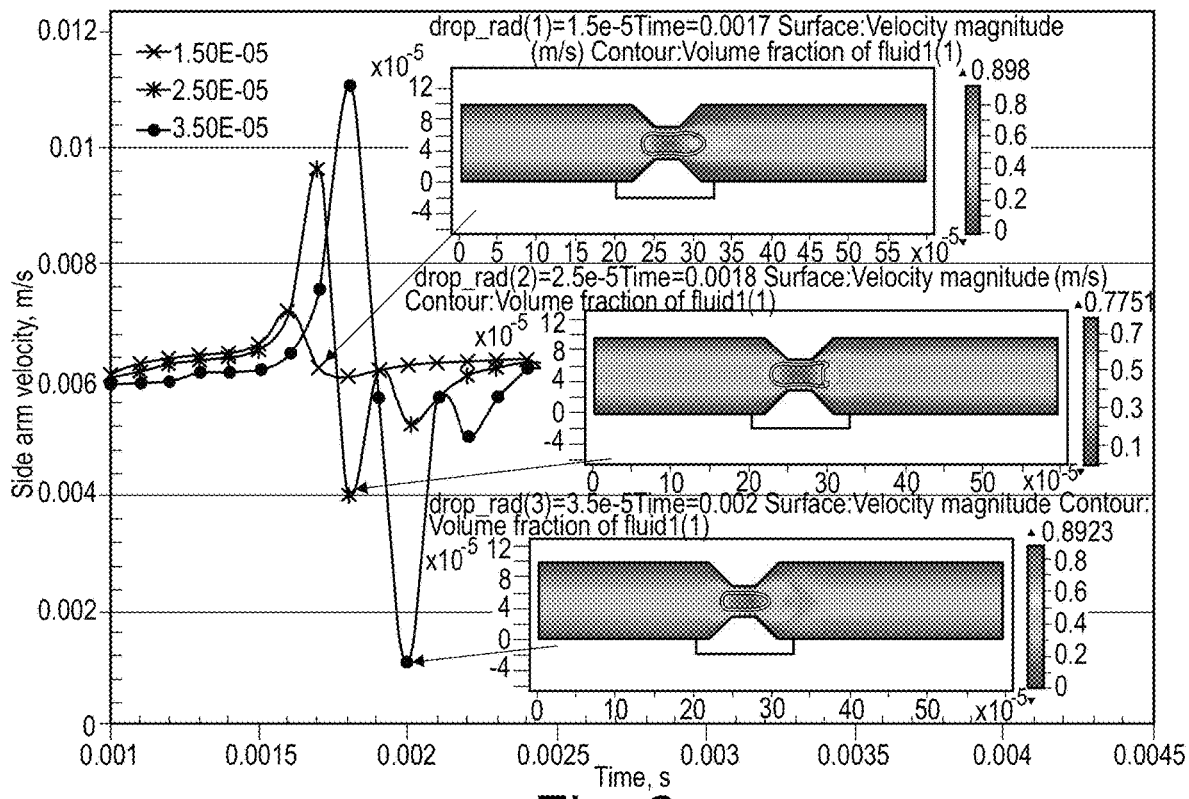
FIG. 2 is another chart of pressure difference across a constriction versus time, in accordance with an embodiment of the present invention.

A similar calculation was carried out for a variation of drop size (see FIG. 2). Again it was found that there is a relation between drop size (most probably relative to the constriction size) and the observed perturbation. Thus, a smaller constriction allows for more sensitivity to interfacial tension, but produces a greater pressure drop.

Figure 3:
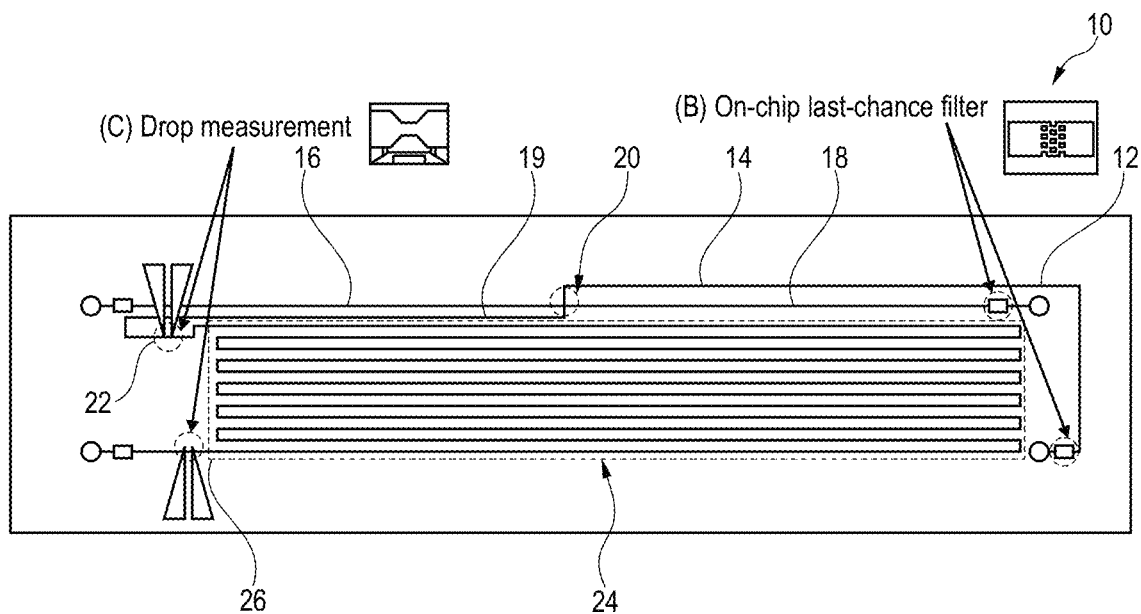
FIG. 3 is schematic layout of a design of microfluidic device according to an embodiment of the present invention.

FIG. 3 shows a plan view of a layout of microfluidic device 10, which is a device according to one embodiment of the present invention. The device 10 comprises flow channels 12 that may be etched into a base material. Merely by way of example, in some embodiments, the flow channels 12 may comprise an etched in the range of 10 of micrometers, for example 50 micrometres or the like.

The device 10 contains an oil channel 14 and water channels 16, 18, which meet at a droplet generator 20 that is configured to form oil-in-water droplets, i.e., oil droplets that are surrounded by and carried along in a water flow. Merely by way of example, the oil droplets may have a diameter of the order of micrometers. For example, in some aspects, the oil droplets may have a diameter having of around 10 micrometres. The generated oil droplet may flow through channel 19. The channels/channel arrangement provided in the figure may be reversed for analyzing water-in-oil droplets, i.e., droplets of water that are surrounded by and carried along in an oil flow, which configuration may be used for analysis of an oil formation. For oil-in-water droplets, the channel walls may be hydrophilic and for water-in-oil droplets, the channel walls may be oleophilic. Moreover, in embodiments of the present invention, the droplet size, for water or oil droplets is adjustable and droplets may be produced of different diameters.

The droplets of oil-in-water are flowed through a first constriction 22, where the interfacial tension of the newly—formed surface is measured according to the present invention. In an embodiment of the present invention, a differential pressure sensor, not shown, is arranged to measure a potential difference across the constriction, between a location upstream of the constriction and a location downstream of the constriction. The droplets of oil-in-water after passing through the constriction then travel along a long channel 24 until they reach a second constriction 26, where the interfacial tension of the aged surface is measured. As in the first constriction 22, a pressure difference sensor (not shown) is used to measure a pressure difference across the second constriction 26 as a droplet passes through the constriction 26.

Figure 4:
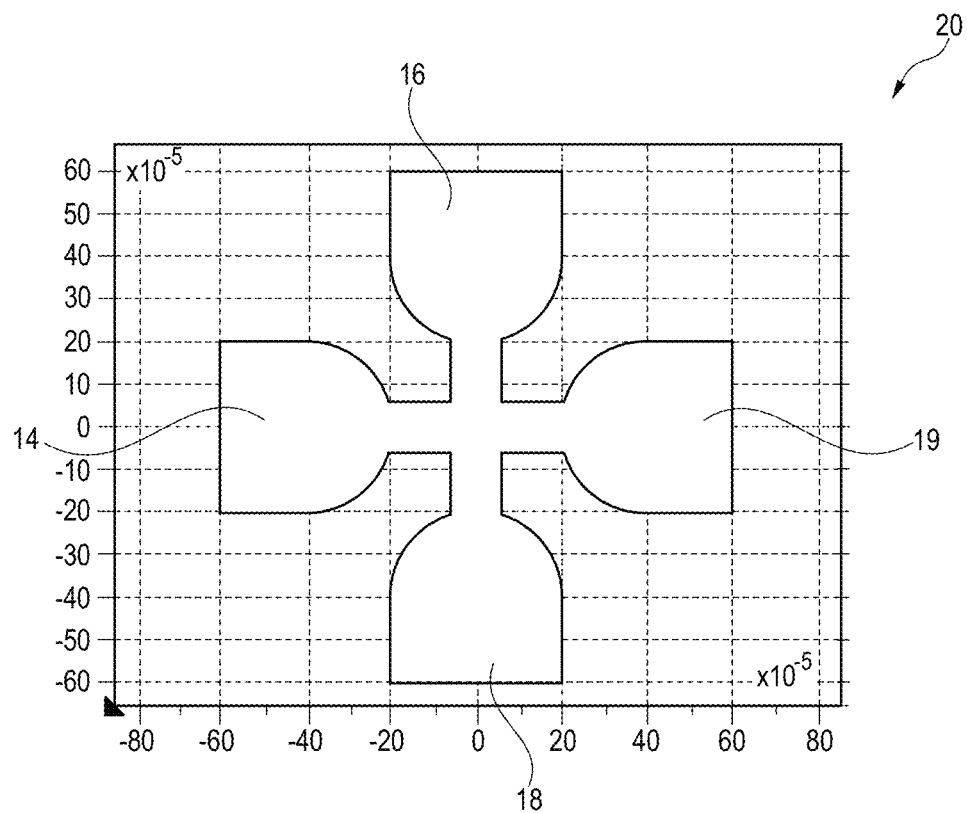
FIG. 4 is a schematic of a droplet generator in a FFD.

FIG. 4 shows a close-up view of droplet generator 20, which shows oil stream 14 meeting two water streams 16, 18 to form stream 19 which is droplets of oil-in-water.

Figure 5:
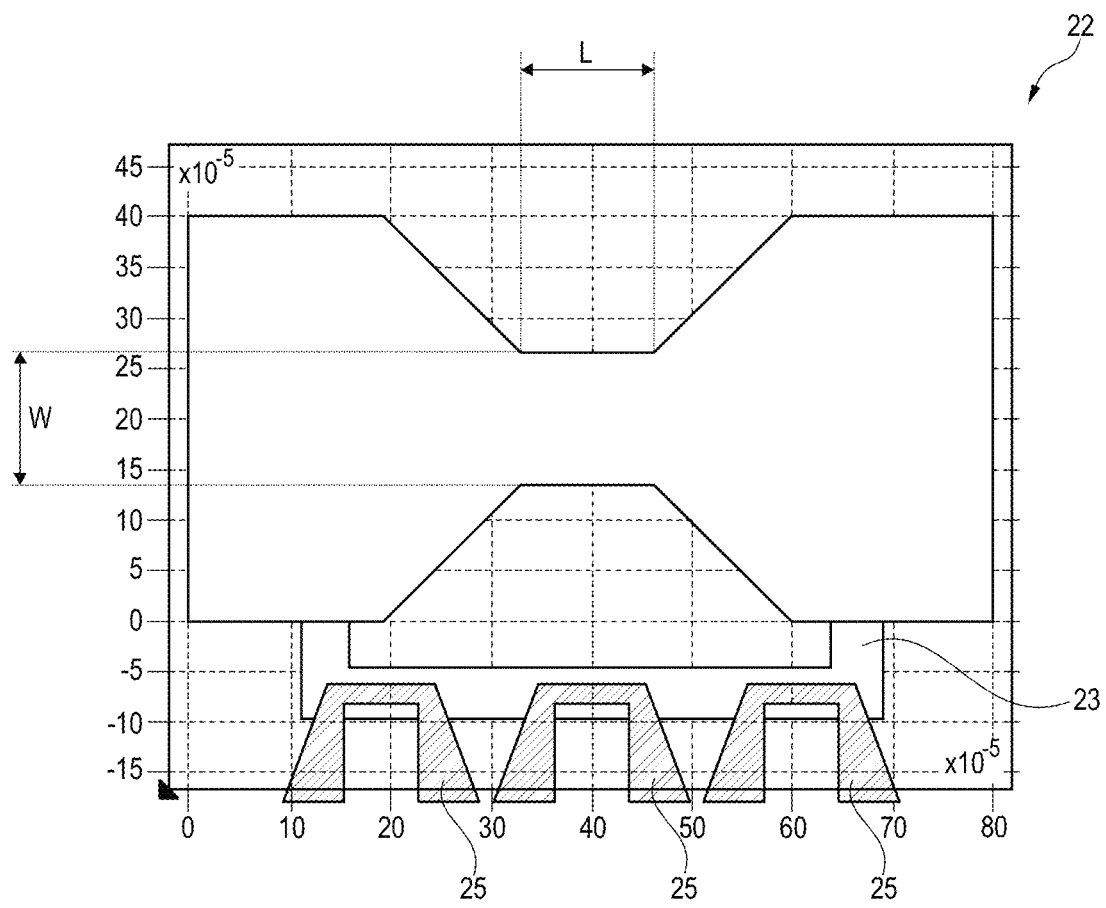
FIG. 5 is a side view of a constriction and a by-pass channel with a flow meter, in accordance with an embodiment of the present invention.

FIG. 5 shows a close-up view of constriction 22. Also shown is a by-pass channel 23 which contains three thin film resistive sensors 25, which measure flow rate and direction according to the degree to which the surrounding fluid is heated.

While the principles of the disclosure have been described above in connection with specific apparatuses and methods, it is to be clearly understood that this description is made only by way of example and not as limitation on the scope of the invention.

What is claimed is:

1. A method of measuring interfacial or surface tension of a first fluid dispersed in a second fluid, the method comprising:
   providing at least one substantially spherical droplet or bubble of the first fluid in a flowing stream of the second fluid in a flow channel;
   passing the flowing stream comprising the second fluid with the droplet or bubble of the first fluid therein through a constriction in the flow channel, wherein the constriction is sufficiently constricting so as to cause the droplet or bubble to deform away from its substantially spherical shape; and
   measuring a difference in pressure of the flowing stream before and after the constriction, wherein the difference in pressure changes as a result of the deformation of the droplet or bubble as it passes through the constriction; and
   determining the interfacial or surface tension of the first fluid from the difference in pressure of the flowing stream before and after the constriction.

2. A method according to claim 1, wherein a by-pass channel is provided around the constriction and the by-pass channel comprises an effective diameter that is smaller than an effective diameter of the constriction.

3. The method according to claim 1, wherein the by-pass channel is sufficiently narrow so that the ratio of volumetric flow through the constriction to the volumetric flow through the by-pass channel is at least 5:1.

4. The method according to claim 1, wherein the ratio of the effective diameter of the constriction to the effective diameter of the by-pass is at least 5:1.

5. The method according to claim 1, which comprises measuring a peak in the pressure difference across the constriction as the droplet or bubble passes through the constriction.

6. The method according to claim 1, wherein the first fluid and the second fluid comprise naturally occurring oil-in-water or water-in-oil mixtures obtained from an underground formation.

7. The method according to claim 1, wherein the droplet or bubble size is from 0.001 mm to 1 mm.

8. The method according to claim 1, wherein the flow channel has an effective diameter of from 0.04 to 2 mm.

9. The method according to claim 1, carried out in a microfluidic flow-focusing device (FFD) to generate the droplets or bubbles of the first fluid in the second fluid.

10. The method according to claim 1, further comprising flowing the second fluid with the droplet or bubble therein through a second constriction that is disposed downstream from the first constriction and measuring a difference in pressure of the flowing stream before and after the second constriction.

11. The method according to claim 1, wherein the by-pass channel is sufficiently narrow so that the ratio of volumetric flow through the constriction to the volumetric flow through the by-pass channel is at least 50:1.

12. The method according to claim 1, wherein the ratio of the effective diameter of the constriction to the effective diameter of the by-pass is at least 10:1.

13. The method according to claim 1 further comprising measuring a flow velocity of the second fluid in the by-pass channel.

14. An interfacial or surface tension measuring apparatus, comprising:
    a flow channel;
    a substantially spherical droplet or bubble generator configured to generate at least one substantially spherical droplet or bubble of a first fluid in a second fluid flowing in the flow channel; the flow channel comprising:
    a first constriction in the flow channel downstream of the droplet or bubble generator, wherein the first constriction comprises an effective diameter that is sufficiently constricting so as to cause the droplet or bubble to deform away from its substantially spherical shape; and
    a first differential pressure sensor configured to measure a differential pressure between measuring points upstream and downstream of the constriction.

15. The apparatus according to claim 14, wherein the first fluid and the second fluid comprise naturally occurring oil-in-water or water-in-oil mixtures obtained from an underground formation.

16. The apparatus according to claim 14, wherein the flow channel has an effective diameter of from 0.04 to 2 mm.

17. The apparatus according to claim 14, wherein the device comprises a microfluidic flow-focusing device (FFD) that is configured to generate the droplets or bubbles of the first fluid in the second fluid.

18. The apparatus according to claim 14, further comprising:
    a second constriction disposed downstream from the first constriction wherein the second constriction comprises an effective diameter that is sufficiently constricting so as to cause the droplet or bubble to deform away from its substantially spherical shape; and
    a second differential pressure sensor configured to measure a differential pressure between measuring points upstream and downstream of the second constriction.

19. The apparatus according to claim 14, further comprising:
    a flowmeter for measuring a flow velocity of the second fluid in the flow channel.

20. The apparatus according to claim 14, further comprising:
    a processor configured to process the interfacial or surface tension of the first fluid.

21. The apparatus according to claim 14, wherein the ratio of the effective diameter of the constriction to the internal diameter of the by-pass is at least 10:1.

22. The apparatus according to claim 14, wherein the flow channel has an effective diameter of from 0.04 to 0.2 mm.

23. An interfacial or surface tension measuring apparatus, comprising:
    a flow channel;
    a substantially spherical droplet or bubble generator configured to generate at least one substantially spherical droplet or bubble of a first fluid in a second fluid flowing in the flow channel; the flow channel comprising:
    a first constriction in the flow channel, wherein the first constriction comprises an effective diameter that is sufficiently constricting so as to cause the droplet or bubble to deform away from its substantially spherical shape;
    a measuring device to measure a physical property of the flowing stream upstream and downstream of the constriction; and
    a by-pass channel configured to flow the second fluid around the constriction, wherein the by-pass channel comprises an internal diameter that is smaller than the effective diameter of the constriction.

24. The apparatus according to claim 23, wherein the ratio of the effective diameter of the constriction to the internal diameter of the by-pass is at least 5:1.

25. The apparatus according to claim 23, further comprising:
    a flowmeter for measuring a flow velocity of the second fluid in the by-pass channel.

* * * * *